(12) United States Patent
Sharma et al.

(10) Patent No.: US 7,186,846 B2
(45) Date of Patent: Mar. 6, 2007

(54) PROCESS FOR PREPARING A DIPEPTIDYL PEPTIDASE IV INHIBITOR AND INTERMEDIATES EMPLOYED THEREIN

(75) Inventors: Padam N. Sharma, Manlius, NY (US); Edward J. Gublo, Liverpool, NY (US); Gabriel M. Galvin, Maple Valley, WA (US); Susan D. Boettger, Fayetteville, NY (US); Saibaba Racha, Fayetteville, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 100 days.

(21) Appl. No.: 11/091,183

(22) Filed: Mar. 28, 2005

(65) Prior Publication Data

US 2005/0222242 A1 Oct. 6, 2005

Related U.S. Application Data

(60) Provisional application No. 60/558,014, filed on Mar. 31, 2004.

(51) Int. Cl.
C07C 69/013 (2006.01)
C07D 209/52 (2006.01)
(52) U.S. Cl. .................................. 548/452; 560/227
(58) Field of Classification Search ............. 548/452; 560/227
See application file for complete search history.

(56) References Cited

U.S. PATENT DOCUMENTS

| 6,068,991 A | 5/2000 | Liu et al. |
| 6,395,767 B2 | 5/2002 | Robl et al. |
| 2005/0090539 A1 | 4/2005 | Vu et al. |

FOREIGN PATENT DOCUMENTS

EP 0 808 824 11/1997

(Continued)

OTHER PUBLICATIONS

U.S. Appl. No. 11/104,015, filed Apr. 12, 2005, Politino, et al.

(Continued)

*Primary Examiner*—Joseph K. McKane
*Assistant Examiner*—Jason M. Nolan
(74) *Attorney, Agent, or Firm*—Burton Rodney

(57) ABSTRACT

A process is provided for preparing a dipeptidyl peptidase IV inhibitor of the structure

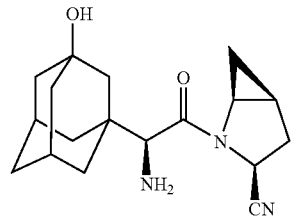

wherein

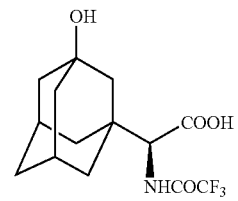

is treated with TFAA in isopropyl acetate to protect the tertiary hydroxyl group as a trifluoroacetate group to form 4

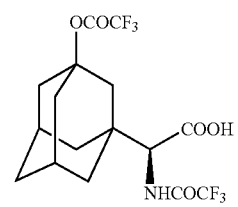

(which is a novel intermediate)
which is converted to acid chloride compound 5

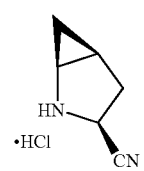

(which is a novel compound)
using Vilsmeier reagent or other chloro reagent and coupled with compound 6 in a heterogeneous mixture of ethyl acetate and aqueous bicarbonate to give compound 7

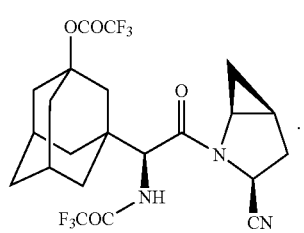

The N,O-bis(trifluoroacetyl) groups of compound 7 are deprotected to give free base compound 10.

1 Claim, No Drawings

FOREIGN PATENT DOCUMENTS

WO     WO 00/04179     1/2000

OTHER PUBLICATIONS

Hanessian, S. et al., "Probing the Importance of Spacial and Conformational Domains in Captopril Analogs for Angiotensin Converting Enzyme Activity", Bioorganic & Medicinal Chemistry Letters, vol. 8, pp. 2123-2128 (1998).

Hanson, R.L. et al., Synthesis of allysine ethylene acetal using phenylalanine dehydrogenase from *Thermoactinomyces intermedius*, Enzyme and Microbial Technology, vol. 26, pp. 348-358 (2000).

Imashiro, R. et al., "Asymmetric synthesis of methyl (2R,3S)-3-(4-methoxyphenyl) glycidate, a key intermediate of diltiazem, via Mukaiyama aldol reaction", Tetrahedron Letters, vol. 42, pp. 1313-1315 (2001).

Reetz, M.T. et al., "General Synthesis of Potentially Antiviral α-Adamantyl Carbonyl Compounds", Angew. Chem. Int. Ed. Engl., vol. 18, No. 1, p. 72 (1979).

Reetz, M.T. et al., "Lewis-Säure-bedingte α-*tert*-Alkylierung von Carbonsäuren und Carbonsäureestern", Chem. Ber., vol. 116, pp. 3708-3724 (1983).

Reetz, M.T. et al., "Regioselektive Lewis-Säure-bedingte α-*tert*-Alkylierung von Acyloinen und Glycolsäure", Chem. Ber., vol. 116, pp. 3702-3707 (1983).

Sagnard, I. et al., "Enantioselective Synthesis of Cyclopropane α-Amino Acids: Synthesis of N-Boc-*cis*-(2S,3R,4S)-3,4-Methanoproline and N-Boc-(2S,3R,4S)-3,4-Methanoglutamic Acid", Tetrahedron Letters, vol. 36, No. 18, pp. 3148-3152 (1995).

Takada, H. et al., "Thermostable Phenylalanine Dehydrogenase of *Thermoactinomyces intermedius*: Cloning, Expression, and Sequencing of Its Gene", J. Biochem., vol. 109, pp. 371-376 (1991).

Tverezovsky, V.V. et al., "Synthesis of (2S, 3R, 4S)-3,4-Methanoproline and Analogues by Cyclopropylidene Insertion", Tetrahedron, vol. 53, No. 43, pp. 14773-14792 (1997).

U.S. Appl. No. 11/119,552, filed May 2, 2005, Patel et al.

U.S. Appl. No. 11/135,217, filed May 23, 2005, Sharma.

PROCESS FOR PREPARING A DIPEPTIDYL PEPTIDASE IV INHIBITOR AND INTERMEDIATES EMPLOYED THEREIN

This application claims a benefit of priority from U.S. Provisional Application No. 60/558,014, filed Mar. 31, 2004, the entire disclosure of which is herein incorporated by reference.

FIELD OF THE INVENTION

The present invention relates to a process for preparing a cyclopropyl-fused pyrrolidine-based dipeptidyl peptidase IV inhibitor and to intermediates produced therein.

BACKGROUND OF THE INVENTION

Dipeptidyl peptidase IV is a membrane bound non-classical serine aminopeptidase which is located in a variety of tissues including, but not limited to, intestine, liver, lung, and kidney. This enzyme is also located on circulating T-lymphocytes wherein it is referred to as CD-26. Dipeptidyl peptidase IV is responsible for the metabolic cleavage of the endogenous peptides GLP-1(7–36) and glucagons in vivo and has demonstrated proteolytic activity against other peptides such as GHRH, NPY, GLP-2 and VIP in vitro.

GLP-1(7–36) is a 29 amino acid peptide derived from post-translational processing of proglucagon in the small intestine. This peptide has multiple actions in vivo. For example, GLP-1(7–36) stimulates insulin secretion and inhibits glucagon secretion. This peptide promotes satiety and slows gastric emptying. Exogenous administration of GLP-1(7–36) via continuous infusion has been shown to be efficacious in diabetic patients. However, the exogenous peptide is degraded too rapidly for continual therapeutic use.

Inhibitors of dipeptidyl peptidase IV have been developed to potentiate endogenous levels of GLP-1(7–36). U.S. Pat. No. 6,395,767 discloses cyclopropyl-fused pyrrolidine-based inhibitors of dipeptidyl peptidase IV. Methods for chemically synthesizing these inhibitors are disclosed in U.S. Pat. No. 6,395,767 as well as in the literature. For example, see Sagnard et al. Tet-Lett. 1995 36:3148–3152; Tverezovsky et al. Tetrahedron 1997 53:14773–14792; and Hanessian et al. Bioorg. Med. Chem. Lett. 1998 8:2123–2128. Inhibitors disclosed in U.S. Pat. No. 6,395,767 include (1S,3S,5S)-2-[(2S)-2-amino-2-(3-hydroxytricyclo[3.3.1.1[3,7]]dec-1-yl)-1-oxoethyl]-2-azabicyclo[3.1.0]hexane-3-carbonitrile, benzoate (1:1) as depicted in Formula M.

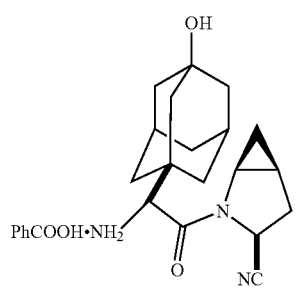

M and the corresponding free base, (1S,3S,5S)-2-[(2S)-2-amino-2-(3-hydroxy-tricyclo[3.3.1.1[3,7]]dec-1-yl)-1-oxoethyl]-2-azabicyclo-[3.1.0]hexane-3-carbonitrile (M') and its monohydrate (M")

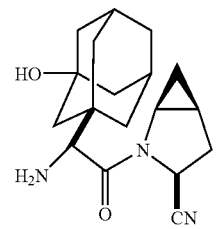

M' free base M' or its monohydrate M"

Methods adapted for preparing intermediates used in the production of this dipeptidyl peptidase IV inhibitor are disclosed in EP 0 808 824 A2. Also see Imashiro and Kuroda Tetrahedron Letters 2001 42:1313–1315, Reetz et al. Chem. Int. Ed. Engl. 1979 18:72, Reetz and Heimbach Chem. Ber. 1983 116:3702–3707, Reetz et al., Chem. Ber. 1983 116: 3708–3724.

The present invention provides new methods and compounds for use in the production of cyclopropyl-fused pyrrolidine-based inhibitors of dipeptidyl peptidase IV.

BRIEF DESCRIPTION OF THE INVENTION

In accordance with the present invention a process is provided for preparing a dipeptidyl peptidase IV (DPP IV) inhibitor having the structure

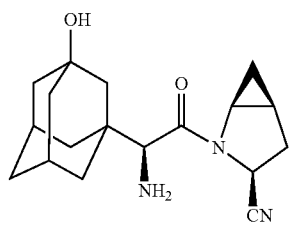

10 which process includes the steps of
(a) providing protected compound 4

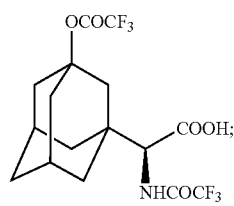

4

(b) treating compound 4 with Vilsmeier reagent or other chloro reagent such as oxalyl chloride-DMF, thionyl chloride-DMF or PCl$_5$ to form the corresponding acid chloride having the structure 5

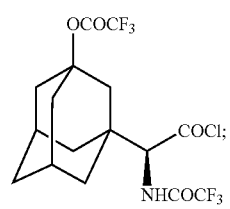

5

(c) treating the acid chloride 5 with a compound having the structure 6

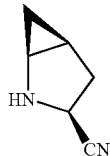

6 or a salt thereof,
to form the diastereomer 7

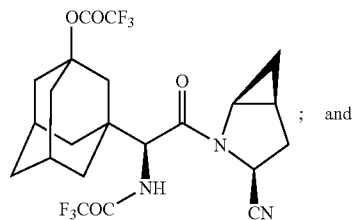

7 and (d) deprotecting the N,O-bis(trifluoroacetyl) groups of compound 7 to form compound 10.

Step (a) in the above reaction for forming compound 4 is a novel process step unto itself in accordance with the present invention.

Step (b) in the above reaction for forming compound 5 is a novel process step unto itself in accordance with the present invention.

Step (c) in the above reaction for treating acid chloride 5 with the HCl salt 6 to form diastereomer 7 is a novel process unto itself in accordance with the present invention.

Step (d) in the above reaction for deprotecting compound 7 to form compound 10 is a novel process unto itself in accordance with the present invention.

The term "Vilsmeier Reagent (or reagent)" refers to (chloromethylene)dimethylammonium chloride which has the structure

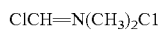

In the above reaction to form the diastereomer 7, the diastereomer 8

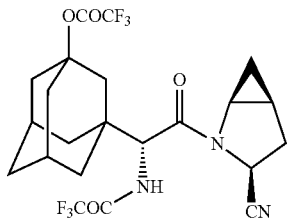

8 is also formed which is separated from the diastereomer 7 by crystallizing out diastereomer 8. The diastereomer 8 may be recovered and deprotected of N,O-bis(trifluoroacetyl) groups to form compound 10a

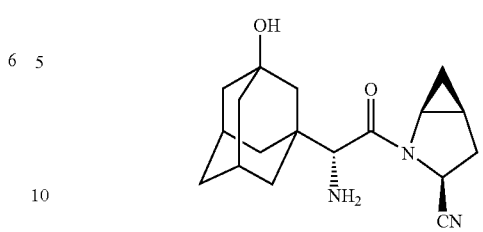

10a which may be employed as a DPP IV inhibitor.

In accordance with the present invention, a process is provided for preparing compound 4 which include the steps of (a) treating a compound of structure 3

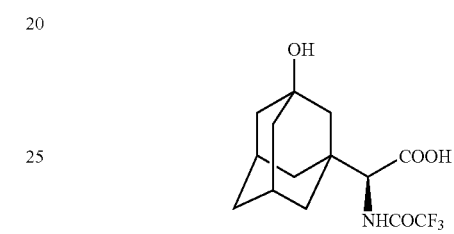

3 with trifluoroacetic anhydride (TFAA); or (b) treating an HCl salt of the structure 2

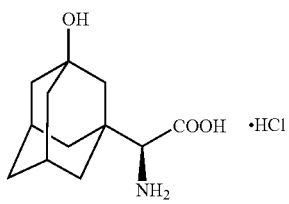

2 with TFAA; or (c) treating a free base of the structure 1

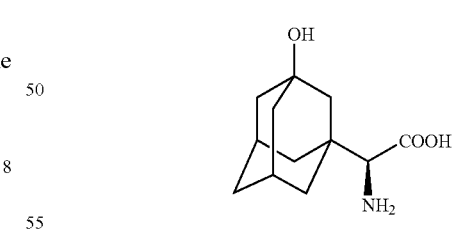

1 with TFAA; or (d) treating free base compound 1 with $CH_3(CH_2)_{11}SCOCF_3$ in basic aqueous solution to cause the free base compound 1 to be protected as its trifluoroacetamide and form compound 3, dissolving the protected compound 3 in an organic solvent and treating the resulting solution with TFAA to form compound 4.

The free base compound 1 and its HCl salt 2 may be prepared as described in U.S. application Ser. No. 10/716,012 filed Nov. 18, 2003 based on Provisional Application No. 60/431,814 filed Dec. 9, 2002.

Further, in accordance with the present invention, a process is provided for preparing compound 3 which includes the step of treating the HCl salt of structure 2

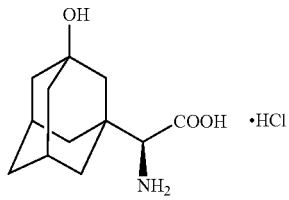

2 with ethyl trifluoroacetate in the presence of potassium methoxide to form compound 3.

In addition, a process is provided for preparing a protected DPP IV inhibitor compound of the structure 10

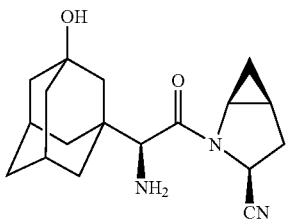

10 which includes the steps of
(a) providing a compound of structure 4

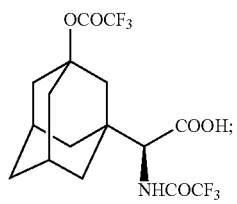

4

(b) treating compound 4 with Vilsmeier reagent or other chloro reagent such as oxalyl chloride-DMF, thionyl chloride-DMF or $PCl_5$ to form acid chloride 5

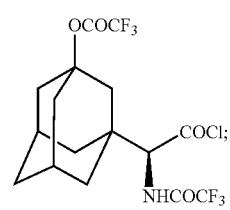

5

(c) treating acid chloride 5 with a compound of the structure 6

6 or a salt thereof (such as the HCl salt)

to form the diastereomer of the structure 7

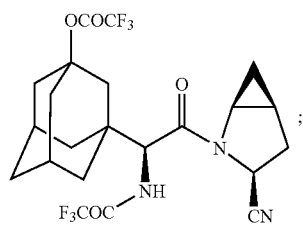

7

(d) treating a solution of compound 7 with sodium bicarbonate to form compound 9 of the structure

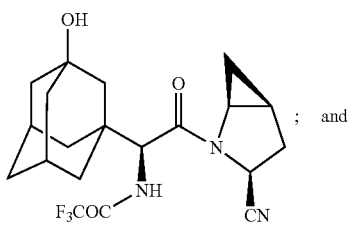

9

; and (e) treating compound 9 with a deprotecting agent to form compound 10.

Compound 6 (free base) is a known compound and is disclosed in U.S. Pat. No. 6,395,767.

In addition, a process is provided for preparing a protected DPP IV inhibitor compound of the structure 10

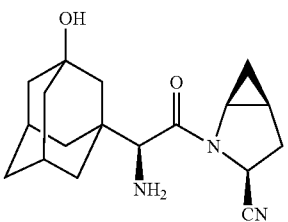

10 which includes the steps of
(a) providing a compound of structure 3

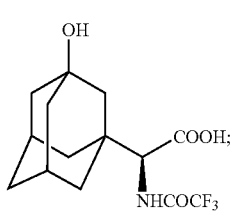

3

(b) treating compound 3 with Vilsmeier reagent or other chloro reagent such as oxalyl chloride-DMF, thionyl chloride-DMF or PCl₅ to form acid chloride 3a

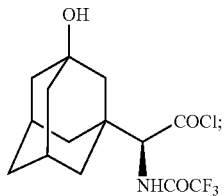

(c) treating acid chloride 3a with a compound of the structure 6

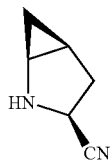

or a salt thereof, to form compound 9 of the structure

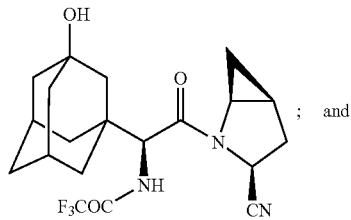

(d) treating compound 9 with a deprotecting agent to form compound 10.

DETAILED DESCRIPTION OF THE INVENTION

The following reaction scheme discloses processes for preparing the dipeptidyl peptidase IV inhibitor 10

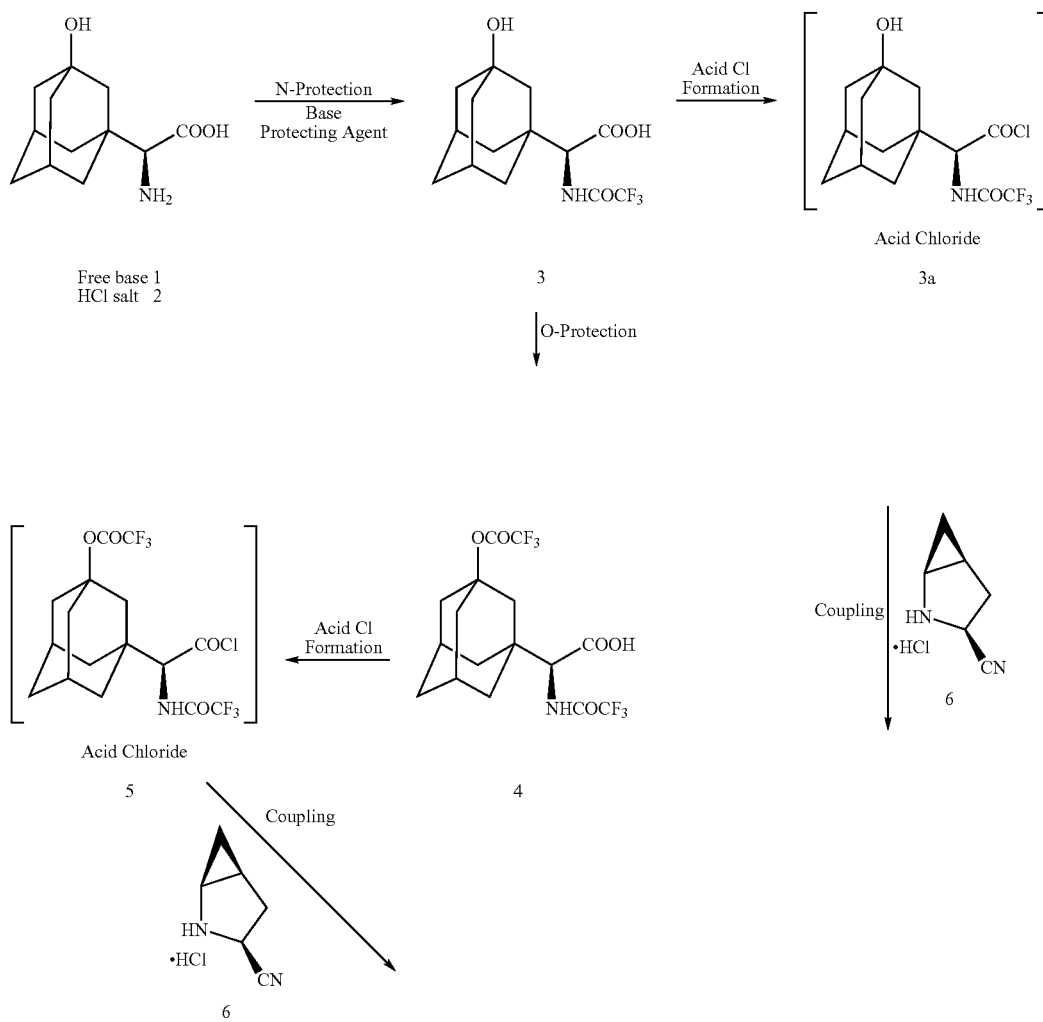

-continued

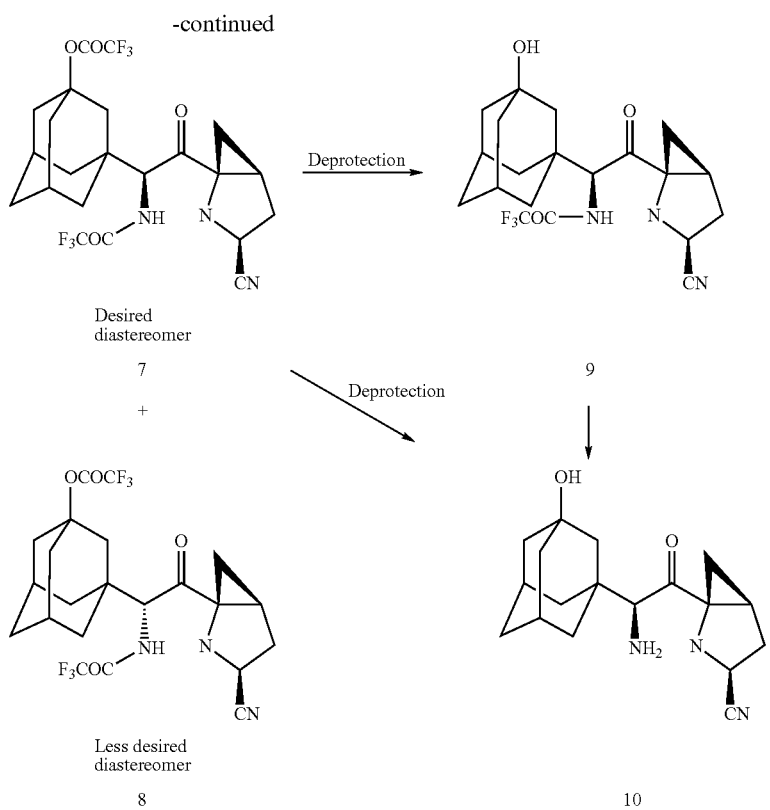

Desired diastereomer
7

+

Less desired diastereomer
8

10

As shown in the reaction scheme, the starting HCl salt 2

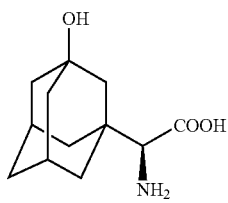

2 is made to undergo N-protection reaction wherein the HCl salt 2 is admixed with a base such as potassium methoxide or other base such as sodium methoxide, lithium methoxide, sodium hydride, potassium hydride, pyridine, triethylamine, N,N-diethylamine, N,N-diisopropylamine, N,N-diisopropylethylamine (Hunig's base), 1, 8-diazabicyclo[5.4.0]undec-7-ene (DBU), 1,5-diazabicyclo[4.3.0]non-5-ene (DBN), or 1,4-diazabicyclo[2.2.2]octane (DABCO) in an organic solvent such as methanol or other solvent such as dichloromethane, toluene, chloroform, THF, acetonitrile, methyl acetate, ethyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, methyl t-butyl ether (MTBE), chlorobenzene, xylenes, heptane, hexanes, cyclohexane, DMF, dimethyl sulfoxide, N-methylpyrrolidinone, ethanol, isopropanol, n-propanol, n-butanol or t-butanol, MTBE, preferably methanol, and the resulting suspension is treated with protecting agent such as ethyl trifluoroacetate or other trifluoroacetate protecting agent such as 1-(trifluoroacetyl)imidazole, trifluoroacetyl chloride, methyl trifluoroacetate, ethyl trifluoroacetate, propyl trifluoroacetate, isopropyl trifluoroacetate, butyl trifluoroacetate, vinyl trifluoroacetate, bismuth (III)trifluoromethanesulfonate or 2-(trifluoroacetoxy)pyridine), preferably ethyl trifluoroacetate, to form protected compound 3

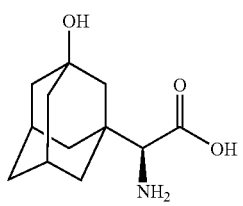

Alternatively, protected compound 3 may be formed by treating free base compound 1

1 with $CH_3(CH_2)_{11}SCOCF_3$ in basic aqueous solution to cause the amino group to be protected as its trifluoroacetamide.

In the reaction of the HCl salt 2 or free base 1 with the protecting agent, the protecting agent will be employed in a molar ratio to the HCl salt 2 or free base 1 within the range from about 1.1 to about 200:1, preferably from about 1.1:1 to about 5:1.

Compound 4 may be prepared from compound 3 via a series of novel processes of the invention as follows:

In a preferred embodiment, compound 3 is dissolved in an organic solvent such as isopropyl acetate or other solvent such as dichloromethane, toluene, chloroform, THF, acetonitrile, methyl acetate, ethyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably isopropyl acetate, and a protecting agent such as TFAA or other trifluoroacetate protecting agent such as 1-(trifluoroacetyl)imidazole, trifluoroacetyl chloride, methyl trifluoroacetate, ethyl trifluoroacetate, propyl trifluoroacetate, isopropyl trifluoroacetate, butyl trifluoroacetate, vinyl trifluoroacetate, bismuth(III)trifluoromethanesulfonate or 2-(trifluoroacetoxy)pyridine), preferably TFAA, is admixed with the solution of compound 3 to form compound 4.

In carrying out the above reaction to form compound 4, the protecting agent will be employed in a molar ratio to compound 3 within the range from about 200:1 to about 1:1, preferably from about 5:1 to about 1:1.

Alternatively, compound 4 may be prepared by reacting HCl salt 2 with a protecting agent such as TFAA or other trifluoroacetate protecting agent such as 1-(trifluoroacetyl) imidazole, 3-(trifluoroacetyl)imidazole, trifluoroacetyl chloride, methyl trifluoroacetate, ethyl trifluoroacetate, propyl trifluoroacetate, isopropyl trifluoroacetate, butyl trifluoroacetate, vinyl trifluoroacetate, bismuth(III)trifluoromethanesulfonate or 2-(trifluoroacetoxy)pyridine), preferably TFAA, to form compound 4. This reaction is carried out employing a molar ratio of TFAA or other protecting agent to compound 2 within the range from about 200:1 to about 1:1, preferably from about 2.1:1 to about 1:1.

In yet another embodiment, compound 4 may be prepared by reacting the free base 1 with a protecting agent such as TFAA or other trifluoroacetate protecting agent such as 1-(trifluoroacetyl)imidazole, trifluoroacetyl chloride, methyl trifluoroacetate, ethyl trifluoroacetate, propyl trifluoroacetate, isopropyl trifluoroacetate, butyl trifluoroacetate, vinyl trifluoroacetate, bismuth(I)trifluoromethanesulfonate or 2-(trifluoroacetoxy)pyridine), preferably TFAA, employing a molar ratio of TFAA or other protecting agent to compound 1 within the range from about 200:1 to about 1:1, preferably from about 2.1:1 to about 1:1.

The diastereomer 7 is prepared from compound 4 by first converting the compound 4 to its corresponding acid chloride 5

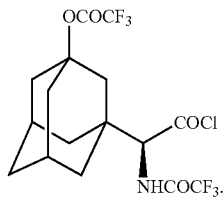

The acid chloride 5 is prepared by dissolving compound 4 in a suitable organic solvent such as ethyl acetate, dichloromethane, toluene, chloroform, THF, acetonitrile, methyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably ethyl acetate, cooling the reaction mixture to a temperature within the range from about −100 to about 200° C., preferably from about −20 to about −25° C., more preferably from about −10 to about −20° C. Vilsmeier reagent ((chloromethylene)dimethylammonium chloride) or other chloro reagent such as oxalyl chloride-DMF, thionyl chloride-DMF or $PCl_5$ is admixed with the compound 4 solution and the reaction mixture is maintained at the above reaction temperature to form acid chloride compound 5.

The above reaction to form acid chloride 5 is carried out employing a molar ratio of Vilsmeier reagent or other chloro reagent to compound 4 within the range from about 200:1 to about 1:1, preferably from about 1.3:1 to about 1:1.

Compound 5 is then coupled to compound 6 or salt thereof as follows:

The compound 6 or a salt thereof, preferably the HCl salt, is dissolved in an organic solvent such as ethyl acetate dichloromethane, toluene, chloroform, THF, acetonitrile, methyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably ethyl acetate, water is added and the solution is cooled to a temperature within the range from about −100 to about 200° C., preferably from about 0 to about 10° C. An aqueous weak base such as $KHCO_3$, $NaHCO_3$, $Na_2CO_3$, $K_2CO_3$, $Li_2CO_3$, $BaCO_3$, $CaCO_3$, $MgCO_3$, KOH, NaOH or LiOH, preferably $KHCO_3$, is admixed with the compound 6 solution which has a pH within the range from about 0 to about 14, preferably about 6 to 7, and the reaction mixture is cooled to a temperature within the range from about −10 to about 200° C., preferably from about 0 to about 5° C. The pH of the reaction mixture is adjusted to within the range from about 0 to about 14, preferably from about 6 to about 7 by the addition of an aqueous base such as $K_2CO_3$, $KHCO_3$, $NaHCO_3$, $Na_2CO_3$, $Li_2CO_3$, $BaCO_3$, $CaCO_3$, $MgCO_3$, KOH, NaOH or LiOH, preferably $K_2CO_3$. The acid chloride 5 solution is admixed with the solution of HCl salt 6 while maintaining the reaction temperature within the range from about −10 to about 200° C., preferably from about 0 to about 5° C., and a pH within the range from about 0 to about 14, preferably from about 6 to about 7 with the addition of aqueous base as described above. In addition to the desired diastereomer 7, the less desired diastereomer 8 is also formed

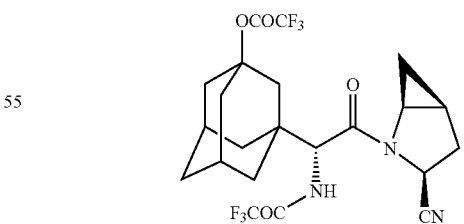

The mixture of desired diastereomer 7 and less desired diastereomer 8 is dissolved in an organic solvent such as toluene, dichloromethane, chloroform, THF, acetonitrile, methyl acetate, ethyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably toluene, and heated to 200° C. preferably to 90° C., and cooled to 10 to 30° C., preferably to 25 to 30° C., and filtered. The filtrate is heated up to 200° C., preferably to 40° C. An organic solvent such as cyclohexane, dichloromethane, toluene, chloroform, THF, acetonitrile, methyl acetate, ethyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, DMF, dimethyl sulfoxide, N-methylpyrrolidinone, ethanol, isopropanol, n-propanol, n-butanol or t-butanol, preferably cyclohexane, is added while maintaining temperature between 35–45° C. This temperature is held for 1 to 24 h, preferably followed by cooling to 20 to 25° C. The reaction is stirred overnight at room temperature and filtered to give a solid desired diastereomer 7.

In carrying out the above reaction to form diastereomer 7, the acid chloride 5 will be employed in a molar ratio to compound 6, preferably HCl salt 6, within the range from about 200:1 to about 1:1, preferably from about 1.2:1 to about 1:1.

The dipeptidyl peptidase IV inhibitor 10 product is prepared from diastereomer 7 as follows:

The diastereomer 7 is suspended in an organic solvent such as ethanol, dichloromethane, toluene, chloroform, THF, acetonitrile, methyl acetate, ethyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, methanol, isopropanol, n-propanol, n-butanol or t-butanol, preferably ethanol, and the suspension is cooled to a temperature within the range from about −100 to about 200° C., preferably from about −10 to about 10° C. A deprotecting agent such as sodium borohydride, potassium borohydride, lithium borohydride, $Et_3BnN^+Br^-$, ammonia, Lewatit 500, barium hydroxide, $PhCH_2N^+Et_3OH^-$, hydrochloric acid, sulfuric acid, nitric acid, trifluoroacetric acid, phosphoric acid, potassium carbonate, potassium bicarbonate, sodium carbonate, sodium bicarbonate, hydrogenation with hydrogen gas, NaOH, KOH or LiOH, preferably sodium borohydride, is added to the reaction mixture while maintaining the reaction at less than 0° C. to form compound 10.

The deprotecting agent is employed in a molar ratio to diastereomer 7 within the range from about 200:1 to about 1:1, preferably from about 1.8:1 to about 1:1.

In another embodiment of the process of the invention as shown, diastereomer 7 is converted to compound 9 which is converted to the compound 10 product.

In preparing compound 9,

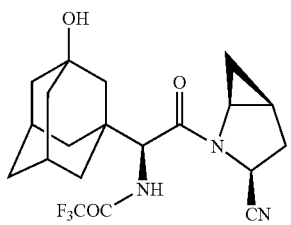

9 the diastereomer 7 is dissolved in an organic solvent such as methanol, dichloromethane, toluene, chloroform, THF, acetonitrile, methyl acetate, ethyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, water, DMF, dimethyl sulfoxide, N-methylpyrrolidinone, ethanol, isopropanol, n-propanol, n-butanol or t-butanol, preferably methanol. A deprotecting agent such as sodium bicarbonate, $KHCO_3$, $Na_2CO_3$, $K_2CO_3$, $Li_2CO_3$, $BaCO_3$ or $CaCO_3$, preferably sodium bicarbonate, is admixed therewith to form compound 9.

The base will be employed in a molar ratio to diastereomer 7 within the range from about 200:1 to about 1:1, preferably from about 2.2:1 to about 1:1.

Compound 9 may be employed to form compound 10 by treating a suspension of compound 9 in an organic solvent such as ethanol, dichloromethane, toluene, chloroform, THF, acetonitrile, 1,2-dimethoxyethane, 2-methyltetrahydrofuran, 1,4-dioxane, MTBE, chlorobenzene, xylenes, heptane, hexanes, cyclohexane, water, DMF, dimethyl sulfoxide, N-methylpyrrolidinone, methanol, isopropanol, n-propanol, n-butanol or t-butanol, preferably ethanol, cooling to a temperature within the range from about −100 to about 200° C., preferably from about −10 to about 10° C., and treating with a deprotecting agent such as sodium borohydride, potassium borohydride, lithium borohydride, $Et_3BnN^+Br^-$, ammonia, Lewatit 500, barium hydroxide, $PhCH_2N^+Et_3OH^-$, hydrochloric acid, sulfuric acid, nitric acid, trifluoroacetric acid, phosphoric acid, potassium carbonate, potassium bicarbonate, sodium carbonate or sodium bicarbonate, hydrogenation with hydrogen gas, NaOH, KOH or LiOH, preferably sodium borohydride, employing a molar ratio of deprotecting agent 9 within the range from about 200:1 to about 0.5:1, preferably from about 0.9:1 to about 1:1, and a reaction temperature within the range from about −100 to about 200° C., preferably from about 0 to about 5° C.

Compound 9 may also be prepared from Compound 3 through acid chloride 3a as follows:

The acid chloride 3a is prepared by dissolving compound 3 in a suitable organic solvent such as ethyl acetate, dichloromethane, toluene, chloroform, THF, acetonitrile, methyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably ethyl acetate, cooling the reaction mixture to a temperature within the range from about −100 to about 200° C., preferably from about −20 to about −25° C., more preferably from about −10 to about −20° C. Vilsmeier reagent ((chloromethylene)dimethylammonium chloride) or other chloro compound reagent, such as oxalyl chloride-DMF, thionyl chloride-DMF or $PCl_5$ is admixed with the compound 3 solution and the reaction mixture is maintained at the above reaction temperature to form acid chloride compound 3a.

The above reaction to form acid chloride 3a is carried out employing a molar ratio of Vilsmeier reagent or other chloro reagent to compound 3 within the range from about 200:1 to about 1:1, preferably from about 1.3:1 to about 1:1.

Compound 3a is then coupled to compound 6 or salt thereof as follows:

The compound 6 or a salt thereof, preferably the HCl salt, is dissolved in an organic solvent such as ethyl acetate, dichloromethane, toluene, chloroform, THF, acetonitrile, methyl acetate, isopropyl acetate, propyl acetate, butyl acetate, acetone, methyl isobutyl ketone, methyl ethyl ketone, 1,2-dimethoxyethane, 2-methyltetrahydrofuran, 1,4-dioxane, MTBE, chlorobenzene, xylenes, heptane, hexanes, cyclohexane, DMF, dimethyl sulfoxide, N-methylpyrrolidinone, ethanol, isopropanol, n-propanol, n-butanol or t-butanol, preferably ethyl acetate, water is added to it, and the solution is cooled to a temperature within the range from about −100 to about 200° C., preferably from about 0 to about 10° C. An aqueous base such as $KHCO_3$, $NaHCO_3$, $Na_2CO_3$, $K_2CO_3$, $Li_2CO_3$, $BaCO_3$, $CaCO_3$, $MgCO_3$, KOH, NaOH or LiOH, preferably $KHCO_3$, is admixed with the compound 6 solution which has a pH within the range from about 0 to about 14, preferably about 6 to 7, and the reaction mixture is cooled to a temperature within the range from about −10 to about 200° C., preferably from about 0 to about 5° C. The pH of the reaction mixture is adjusted to within the range from about 0 to about 14, preferably from about 6 to about 7, by the addition of an aqueous base such as $K_2CO_3$, $KHCO_3$, $NaHCO_3$, $Na_2CO_3$, $Li_2CO_3$, $BaCO_3$, $CaCO_3$, $MgCO_3$, KOH, NaOH or LiOH, preferably $K_2CO_3$. The acid chloride 3a solution is admixed with the solution of HCl salt 6 while maintaining the reaction temperature within the range from about −10 to about 200° C., preferably from about 0 to about 5° C., and a pH within the range from about 0 to about 14, preferably from about 6 to about 7, with the addition of aqueous base as described above to give compound 9.

In carrying out the above reaction to form compound 9, the acid chloride 3a will be employed in a molar ratio to compound 6, preferably the HCl salt of 6, within the range from about 200:1 to about 1:1, preferably from about 1.2:1 to about 1:1.

In addition, in accordance with the present invention, the following compounds are novel intermediates:

(a) 4

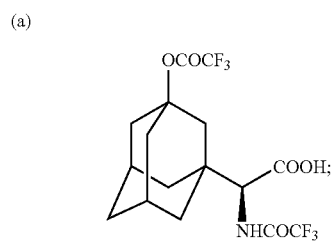

(b) 7

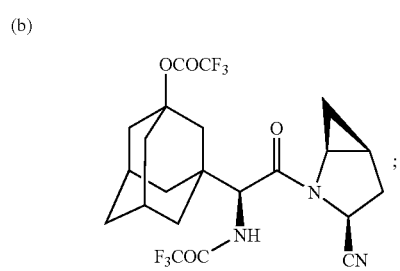

(c) 8

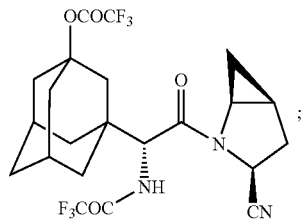

(d) 9

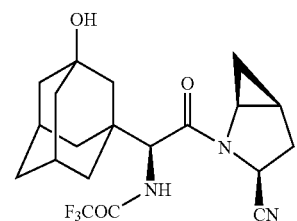

Compound 10 is an inhibitor of dipeptidyl peptidase IV and thus is useful in the treatment of diabetes and complications thereof, hyperglycemia, Syndrome X, hyperinsulinemia, obesity, and atherosclerosis and related diseases as well as immunomodulatory diseases and chronic inflammatory bowel disease. A full disclosure of utilities for dipeptidyl peptidase IV inhibitors including formulations, dosages, and dosage regimens are disclosed in U.S. Pat. No. 6,395,767 which is incorporated herein by reference.

The following Examples represent preferred embodiments of the invention.

EXAMPLES

Example 1

Preparation of

3

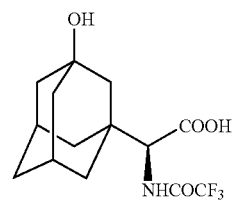

from

2

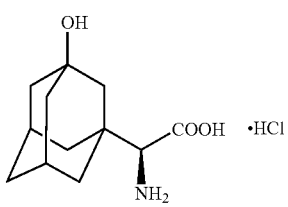

The HCl salt 2 (26.1 g, 1 equiv) was added as a solid in one portion to a suspension of potassium methoxide (22.8 g, 3.1 equiv) in methanol (228 mL). Ethyl trifluoroacetate (29.8 g, 24.9 mL, 2.1 equiv) was added slowly to the reaction mixture and the mixture was stirred at room temperature for 15 minutes. HPLC suggested the completion of reaction. A solution of concentrated HCl (12 g), NaCl (1.44 g) and water (130 mL) was added to the reaction mixture and stirred for 15 minutes. The reaction mixture was concentrated under reduced pressure leaving an aqueous layer. Ethyl acetate (100 mL) was added followed by a solution (100 mL) of conc. HCl (12 g), NaCl (1.44 g) and water (130 mL). The aqueous layer was separated and re-extracted with ethyl acetate (3×50 mL). The combined organic layers were washed with brine (2×50 mL), dried (MgSO$_4$) and filtered. The filtrate was concentrated under reduced pressure to leave an oily residue. The residue was triturated with heptane (100 mL) to give a solid. The solid was filtered and dried at 35° C. under vacuum overnight to give compound 3, 30.0 g, 94% yield, 98% pure, CIMS m/z 339 [M+18 (NH4)]$^+$. ESI: m/z 322 (very weak)(M+H)$^+$, 344 (M+Na)$^+$, 665 (2M+Na)$^+$, 687 (2M–H+2Na)$^+$, 703 (2M–H+K+Na)$^+$, 986 (3M+Na)$^+$, 1008 (3M–H+2Na)$^+$, 1030 (3M–2H+3Na)$^+$. $^1$H and $^{19}$F NMR data were in accordance with the structure for 3.

Example 2

Preparation of

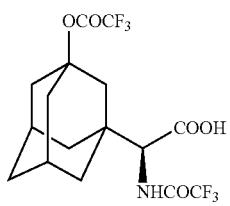

4

A. From

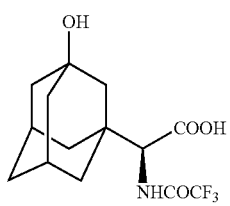

3

TFAA (110 mL) was added to compound 3 (22.8 g) and the resulting solution was stirred at room temperature under nitrogen atmosphere for 2 h until HPLC showed the completion of reaction. The reaction mixture was cooled to −30° C. and quenched by a dropwise addition of water (150 mL) maintaining the reaction temperature below 0° C. (exotherm). The reaction mixture was diluted by the addition of dichloromethane (150 mL) and was stirred for 5 minutes. The organic layer was separated and the aqueous layer was re-extracted with dichloromethane (3×50 mL). The combined organic layers were washed with brine (3×50 mL), dried (MgSO$_4$) and concentrated to leave a residue, 20.3 g, 68.5% crude yield. The residue was purified by column chromatography eluting with a mixture of dichloromethane-methanol (98:2) to give title compound 4, 16.07 g, 96% pure, 54.3% yield. CIMS: m/z 440 (M+Na); ESI: m/z 440 (M+Na)$^+$, 462 (M–H+2Na)$^+$, 879 (2M–H+2Na)$^+$, 895 (2M–H+K+Na)$^+$, 901 (2M–2H+3Na)$^+$. $^1$H and $^{19}$F NMR data were in accordance with the structure for 4.

B. From

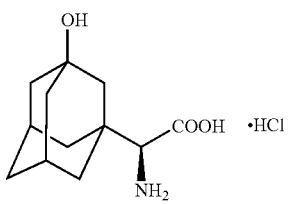

2

Example 1 starting material

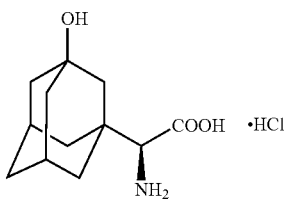

2

(13.3 g) was reacted with TFAA (66 mL) as described above in Part A to give title compound 4, 13 g, 63.5% yield.

C. From

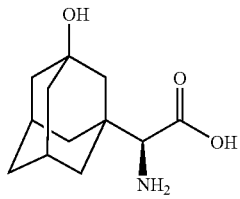

1

Example 1 starting material in the form of its free base 1 (100 mg) was reacted with TFAA (1 mL) as described above to give title compound 4, 185 mg, 80% yield.

Example 3

Direct conversion of

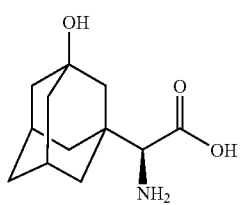

1 reaction mixture to

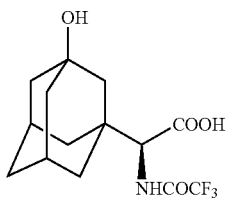

4

A. Preparation of

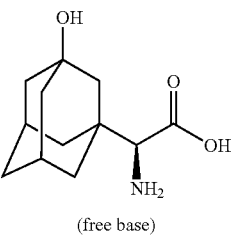

3 from

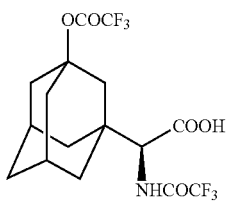

1

(free base)

reaction mixture

A bioconversion mixture (80 mL) containing 8.0 g of free base 1

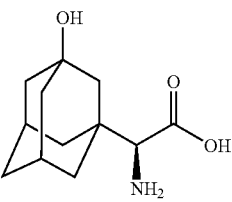

1

(1.0 equiv) was added to a 500-mL flask. THF (80 mL) was added and the pH of the mixture was adjusted to 9.0 using 10 N NaOH. $CH_3(CH_2)_{11}SCOCF_3$ (52.8 g, 5.0 equiv) was then added and the mixture was heated to 55–60° C. The reaction mixture was stirred at 55–60° C. for 5.5 h, until $^1$H NMR indicated the absence of starting material 1 in the reaction mixture. During this time the pH was maintained at 8.5–9.0 using 10 N NaOH. The reaction mixture was cooled to 20–25° C. and THF was removed under vacuum leaving an aqueous layer. Isopropyl acetate (140 mL) was added and the pH of the mixture was adjusted to 2.0 using 35% aq. $H_2SO_4$ followed by the addition of Celite (4 g). The mixture was then filtered through a 4 g pad of Celite and the cake was washed with isopropyl acetate (80 mL). The pH of the filtrate was re-adjusted to 8.0 using 10 N NaOH. The organic layer was separated. Additional isopropyl acetate (150 mL) was added to the aqueous layer and the pH was re-adjusted to 2.0 using 35% aq. $H_2SO_4$. The organic layer was separated. The combined organic layer (191 mL) containing 10.92 g of compound 3 based on HPLC quantitation (95.7% yield from compound 1) was concentrated under reduced pressure. This was dissolved in isopropyl acetate (2×150 mL) and concentrated under reduced pressure to leave a crude residue (13.5 g) containing 10.92 g of compound 3.

$^1$H NMR method for monitoring the reaction: $^1$H NMR was utilized to determine the relative ratio of compound 1 and compound 3 by comparing the integration of the α-amino proton signals. 10 μL of the reaction mixture was dissolved in a 1:2 mixture of $CD_3CN$-$D_2O$. The α-amino proton signal for compound 1 appears at 3.28 ppm. The α-amino proton signal for compound 3 appears at 4.1 ppm.

This reaction can also be carried out in other solvents such as DMF and MeCN.

B. Preparation of

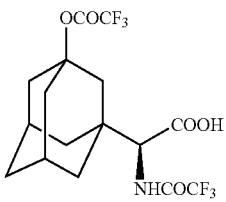

4 from crude

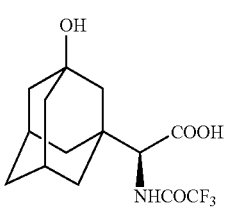

3

The crude product residue of compound 3 obtained from Part A (13.5 g) containing 10.92 g of compound 3 was dissolved in isopropyl acetate (54.6 mL). TFAA (21.8 mL, 4.5 equiv) was added to it in one portion (exotherm to 33° C.). The reaction mixture was stirred at room temperature for 1.5 h. HPLC showed the absence of compound 3 in the reaction mixture. The reaction mixture was cooled to <0° C. and quenched by dropwise addition of water (55 mL), while maintaining reaction mixture temperature at <10° C. The quenched reaction mixture was stirred at −5 to 5° C. for 45 minutes. The organic layer was separated and washed with water (3×50 mL). The combined aqueous layers were re-extracted with isopropyl acetate (2×10 mL). The combined organic layers were concentrated under reduced pressure at <57° C. to leave a residue. The residue was taken up in dichloromethane (11 mL) and heated to 35° C. Heptane (220 mL) was added slowly while maintaining temperature between 50 to 55° C. to crystallize a solid. This mixture was cooled to room temperature and stirred at room temperature for 3.5 h. The solid was filtered, washed with heptane (3×15 mL) and dried at 50° C. under vacuum overnight to give compound 4, 12.1 g, 98.0% pure, 85.3% yield from compound 3 and 81.6% yield from compound 1.

Example 4

Preparation of

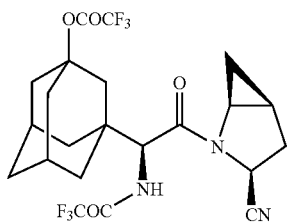

from

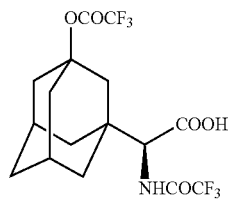

A. Acid Chloride Preparation

Compound 4 (20 g, 1 equiv) was dissolved in ethyl acetate (240 mL). The reaction mixture was cooled to −15 to −20° C. Vilsmeier reagent (7.97 g, 1.3 equiv) was added in one portion and the reaction mixture was stirred at −15 to −20° C. for 2 h until HPLC showed the disappearance of compound 4. An aliquot of the reaction mixture was quenched with a 0.24 M solution of N,N-diethylamine in acetonitrile to form the corresponding amide. HPLC showed >92% of N,N-diethylamide.

B. Coupling with

Compound 6 (8.3 g, 1.2 equiv) was taken up in ethyl acetate (95 mL) in a separate vessel and cooled to 0 to 10° C. A solution of KHCO$_3$ (5.8 g, 1.2 equiv) in water (193 mL) was added to the ethyl acetate solution and the reaction mixture was cooled to 0 to 5° C. (initial pH 5.6). The pH was adjusted to 6.8 by the addition of 10% aqueous K$_2$CO$_3$ (15 mL). The acid chloride reaction mixture from Example 4, step A was added to this reaction mixture, while maintaining the reaction temperature between 0 to 5° C. and the pH between 6 and 7 by the simultaneous addition of 10% aqueous K$_2$CO$_3$ (80 mL). The reaction was stirred at 0 to 5° C. for 15 minutes. The HPLC showed disappearance of compound 4. The reaction mixture was warmed to room temperature.

The organic layer was separated and washed with water (200 mL), 1 M aqueous H$_3$PO$_4$ (200 mL) and water (200 mL). The organic layer was concentrated under reduced pressure to a residue, which was suspended in toluene (40 mL) and concentrated to leave an oily residue. The oily residue was suspended again in toluene (40 mL), heated to 90° C. and cooled to 25 to 30° C. The resulting suspension was filtered and the solid was dried at 53° C. overnight to give 4.2 g of a dry solid. The solid contained a 41.7:58.3 ratio of the less desired diastereomer 8 to the desired diastereomer compound 7 by HPLC.

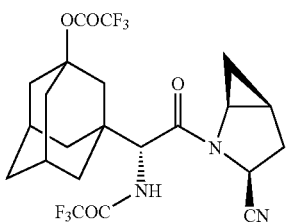

The filtrate, which contained 0.13% of the less desired diastereomer 8 by HPLC, was heated to 40° C. Cyclohexane (120 mL) was added, while maintaining the temperature between 35 and 40° C. The mixture was heated at 35–40° C. for 2 h cooled to 20–25° C., and stirred overnight at room temperature to precipitate a solid. The solid was filtered, washed with cyclohexane (2×20 mL) and dried at 50–55° C. under vacuum overnight to give compound 7, 16.1 g, 66.3% yield, 98.6% pure, 0.09% of less desired diastereomer 8 and 5.3% toluene by $^1$H NMR. MS (ESI): m/z 508 (very weak) (M+H)$^+$, 530 (M+Na)$^+$, 546 (M+K)$^+$, 1037 (2M+Na)$^+$, 1053 (2M+K)$^+$. $^1$H and $^{19}$F NMR data were in accordance with the structure for 7.

Example 5

Preparation of

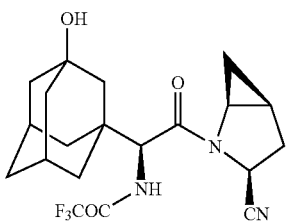

from

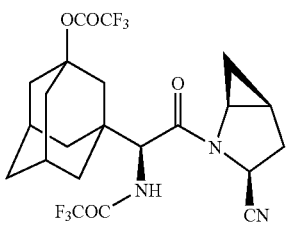

Compound 7 (10.34 g, 1 equiv) was dissolved in methanol (150 mL). Solid sodium bicarbonate (3.41 g, 2.2 equiv) was added to the reaction mixture in one portion. The heterogeneous reaction mixture was stirred at room temperature overnight until HPLC showed the absence of starting material. The reaction mixture was concentrated under vacuum to leave a residue, which was taken up in water (100 mL) and acidified to pH 3–4 by the addition of 1 M aqueous HCl. Dichloromethane (100 mL) was then added and the phases were stirred. The organic layer was separated and the aqueous layer was re-extracted with dichloromethane (2×50 mL). The combined organic layers were concentrated under reduced pressure to a residue, which was dissolved in ethyl acetate (20 mL). The solution was heated to 70° C. and heptane (31 mL) was added slowly while maintaining temperature >70° C. The mixture was stirred at >70° C. for 30 minutes, cooled to room temperature and stirred overnight to crystallize a solid. The solid was filtered, washed with heptane (3×5 mL) and dried at 50° C. overnight under vacuum to give compound 9, 6.77 g, 79.3% yield. MS (ESI) m/z 412 (very weak) (M+H)$^+$, 434 (M+Na)$^+$, 450 (M+K)$^+$, 845 (2M+Na)$^+$. $^1$H and $^{19}$F NMR data were in accordance with the structure for 9.

Example 6

Preparation of

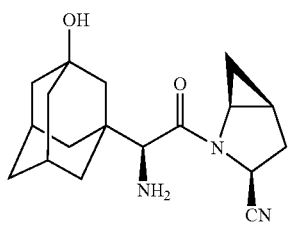

10 from

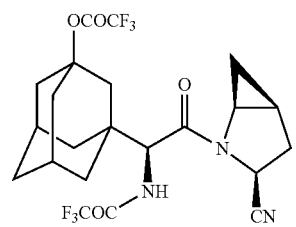

7

Compound 7 (20 g) was suspended in absolute ethanol (100 mL) and cooled to <−4° C. Sodium borohydride (2.84 g, 1.8 equiv) was added to the reaction mixture in several portions, while maintaining reaction temperature <0° C. The reaction mixture was stirred at <0° C. for 15 minutes and then at 0–5° C. (preferably 5° C.) for 4 h until HPLC showed the absence of starting material 7. The reaction mixture was then cooled to <−4° C. and quenched by dropwise addition of water (200 mL), while maintaining reaction temperature <5° C. The pH was adjusted from 11.8 to 2–3 by the addition of 6 N aqueous HCl (16.8 mL). The reaction mixture was stirred at <5° C. overnight. The pH of the reaction mixture was readjusted to 2–3 by the addition of 6 N aqueous HCl. Dichloromethane (500 mL) was then added and the mixture was cooled to <2° C. The pH was carefully adjusted to 9–10 by the addition of 25% aq. sodium hydroxide (9.4 mL) while maintaining reaction temperature <2° C. Sodium chloride (60 g) was added and the pH was readjusted to 9–10 by the addition of 25% aqueous sodium hydroxide solution (1.6 mL). The reaction mixture was stirred at <2° C. for 5 minutes and then warmed to 5° C. The organic layer was separated and the aqueous layer was re-extracted with dichloromethane (2×200 mL). The combined organic layers were washed with 1% ammonium chloride-brine solution (100 mL) and filtered. The filtrate was concentrated to an oily residue and re-filtered, and the solids were rinsed with dichloromethane. The filtrate was diluted with ethyl acetate (12 mL) and concentrated to remove dichloromethane. This process was repeated twice. Ethyl acetate was added to adjust the total volume to 88 mL, and water (1.0 mL, 1.5 equiv) was added dropwise. This mixture was stirred for 15 minutes to crystallize a white solid. Additional water (1.0 mL, 1.5 equiv) was added slowly and the slurry stirred for 4 h at room temperature. The solid was filtered, washed with ethyl acetate (2×4 mL) and dried at 25° C. under vacuum overnight to give compound 10, 8.73 g, 70% yield, 98.5% pure. MS (ESI): m/z 316 (M+H)$^+$, 338 (M+Na)$^+$, 631 (2M+H)$^+$, 653 (2M+Na)$^+$, 946 (3M+H)$^+$, 968 (3M+Na)$^+$. $^1$H and $^{19}$F NMR data were in accordance with the structure for 10.

Example 7

Preparation of free base 10 from

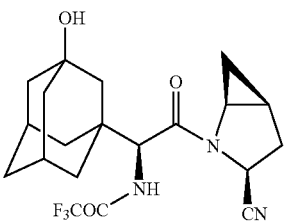

9

The compound 9 from Example 5

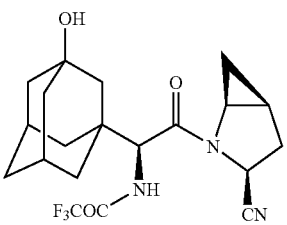

9

What is claimed is:
1. A compound having the structure
(a) 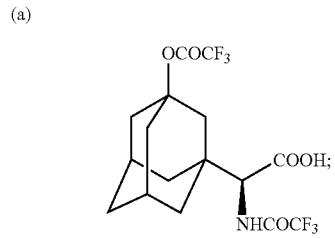
(b) 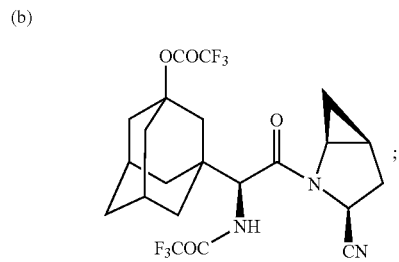
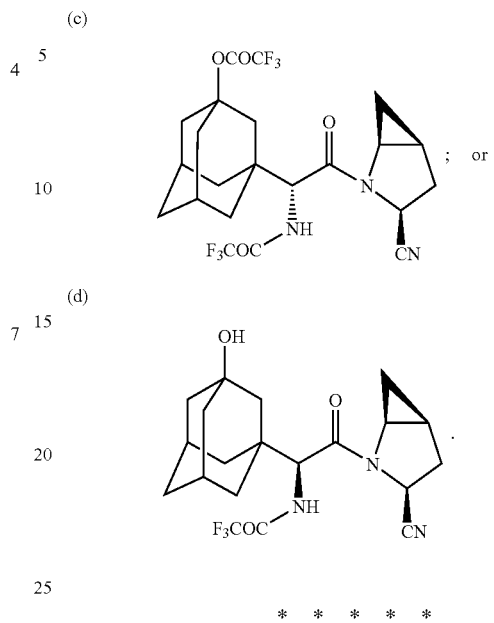

(1 g) was dissolved in absolute ethanol (5 mL) and cooled to <−5° C. Sodium borohydride (0.83 g, 0.9 equiv) was added in several portions, while maintaining reaction temperature <0° C. The reaction mixture was stirred at <0° C. for 15 minutes, warmed to between 0 and 5° C. (preferably 5° C.) and stirred for 3 h. Additional sodium borohydride (0.83 g, 0.9 equiv) was added and the reaction mixture was stirred at 0–5° C. for 4 h, until HPLC showed the absence of starting material 9 in the reaction mixture. The reaction mixture was worked up and crystallized as described in Example 6 above to give the title compound 10, 530 mg, 65% yield.